(12) United States Patent
Eliasson et al.

(10) Patent No.: US 12,186,170 B2
(45) Date of Patent: Jan. 7, 2025

(54) SANITARY ARTICLE COMPRISING SHAPING ELEMENTS

(71) Applicant: Essity Hygiene and Health Aktiebolag, Gothenburg (SE)

(72) Inventors: Louise Eliasson, Gothenburg (SE);
Oscar Lipschutz, Gothenburg (SE);
David Lindqvist, Gothenburg (SE);
Johan Dahlberg, Gothenburg (SE);
Anna-Karin Nyström, Gothenburg (SE)

(73) Assignee: ESSITY HYGIENE AND HEALTH AKTIEBOLAG, Gothenburg (SE)

( * ) Notice: Subject to any disclaimer, the term of this patent is extended or adjusted under 35 U.S.C. 154(b) by 0 days.

(21) Appl. No.: 18/567,836

(22) PCT Filed: Jun. 10, 2021

(86) PCT No.: PCT/EP2021/065649
§ 371 (c)(1),
(2) Date: Dec. 7, 2023

(87) PCT Pub. No.: WO2022/258186
PCT Pub. Date: Dec. 15, 2022

(65) Prior Publication Data
US 2024/0252363 A1    Aug. 1, 2024

(51) Int. Cl.
*A61F 13/15* (2006.01)
*A61F 13/472* (2006.01)
(Continued)

(52) U.S. Cl.
CPC .. *A61F 13/47236* (2013.01); *A61F 13/53747* (2013.01); *A61F 2013/15406* (2013.01); *A61F 2013/4708* (2013.01)

(58) Field of Classification Search
CPC .......... A61F 13/47236; A61F 13/53747; A61F 13/47245; A61F 13/49001;
(Continued)

(56) References Cited

U.S. PATENT DOCUMENTS 2,064,431 A    12/1936  Jurgensen
7,078,583 B2 *  7/2006  Kudo ................ A61F 13/47227
                                               604/385.01
(Continued)

FOREIGN PATENT DOCUMENTS

CN    1081355 A    2/1994
CN    1334710 A    2/2002
(Continued)

OTHER PUBLICATIONS

Chinese Application No. 202180099032.X; First Office Action with English translation dated Mar. 8, 2024; 13 pages.
(Continued)

*Primary Examiner* — Jacqueline F Stephens
(74) *Attorney, Agent, or Firm* — CANTOR COLBURN LLP (57) ABSTRACT

The present disclosure relates to a sanitary article (1), such as a sanitary napkin or a pantiliner, the sanitary article comprising a topsheet (2), a backsheet (3), an acquisition layer (4) and an absorbent core (5), the absorbent core (5) being arranged between the topsheet (2) and the backsheet (3) and the acquisition layer (4) being arranged between the topsheet (2) and the absorbent core (5), the sanitary article (1) having an extension in a longitudinal direction L about a longitudinal centerline U and in a transverse direction T, the sanitary article (1) having first and second longitudinal side edges (6,7) extending in the longitudinal direction L and front and rear transverse side edges (8,9) extending in the
(Continued)

transverse direction T, the sanitary article being divided in a frontmost half (10) and a rearmost half (11), as seen in the longitudinal direction L, wherein the absorbent core (4) in the frontmost half (10) of the sanitary article (1) is provided with a low-density front shaping element (12) having a lower density than an adjacent region of the absorbent core (5), the low-density front shaping element (12) comprising a shaping element first leg section (12*a*) and a shaping element second leg section (12*b*), the frontmost half (10) of the sanitary article (1) furthermore comprising a V-shaped, or modified V-shaped, front embossed element (13) comprising a first embossed leg section (13*a*) and a second embossed leg section (13*b*), wherein the shaping element first leg section (12*a*) and the shaping element second leg section (12*b*) tend towards each other and towards the front transverse side edge (8) of the sanitary article (1) to form a non-intersecting V-shape, the shaping element first leg section (12*a*) and the shaping element second leg section (12*b*) being arranged on a respective side of the longitudinal centerline L of the sanitary article (1), and in that the V-shaped front embossing element (13) is provided only in the topsheet (2) and in the acquisition layer (4) and in that the low-density front shaping element (12) and the V-shaped front embossing element (13) partly or completely overlap each other.

19 Claims, 4 Drawing Sheets

(51) Int. Cl.
*A61F 13/537* (2006.01)
*A61F 13/47* (2006.01)

(58) Field of Classification Search
CPC .......... A61F 13/51108; A61F 13/51104; A61F 2013/15406; A61F 2013/4708; A61F 2013/51078; A61F 2013/49082; A61F 2013/49071
See application file for complete search history.

(56) References Cited

U.S. PATENT DOCUMENTS

| | | | |
|---|---|---|---|
| 10,512,566 B2* | 12/2019 | Park | ................ A61F 13/47272 |
| 2005/0148989 A1 | 7/2005 | Otsubo et al. | |
| 2005/0182374 A1 | 8/2005 | Zander et al. | |
| 2005/0187531 A1 | 8/2005 | Alcantara et al. | |
| 2006/0116652 A1 | 6/2006 | Miura et al. | |
| 2015/0005729 A1 | 1/2015 | Nakao et al. | |
| 2015/0265474 A1 | 9/2015 | Munakata et al. | |
| 2016/0213525 A1 | 7/2016 | Suzuki et al. | |
| 2017/0246045 A1* | 8/2017 | Schmoker | ............. A61F 13/581 |
| 2018/0000661 A1 | 1/2018 | Sanborn et al. | |
| 2018/0140476 A1 | 5/2018 | Lee et al. | |
| 2019/0336359 A1 | 11/2019 | Kuroda | |
| 2020/0138644 A1* | 5/2020 | Hanson | ................ A61F 13/532 |
| 2020/0163809 A1 | 5/2020 | Radne et al. | |
| 2020/0368081 A1 | 11/2020 | Park et al. | |

FOREIGN PATENT DOCUMENTS

| | | |
|---|---|---|
| CN | 1334711 A | 2/2002 |
| CN | 1334712 A | 2/2002 |
| CN | 1929801 A | 3/2007 |
| CN | 101068517 A | 11/2007 |
| CN | 103533916 A | 1/2014 |
| CN | 105455960 A | 4/2016 |
| CN | 106456414 A | 2/2017 |
| CN | 108836637 A | 11/2018 |
| CN | 110709044 A | 1/2020 |
| EP | 3473224 A1 | 4/2019 |
| JP | 2004350908 A | 12/2004 |
| JP | 2007152032 A | 6/2007 |
| JP | 2015051233 A | 3/2015 |
| JP | 2018000466 A | 1/2018 |
| JP | 2018094301 A | 6/2018 |
| WO | 2018226133 A1 | 12/2018 |
| WO | 2022258187 A1 | 12/2022 |

OTHER PUBLICATIONS

Chinese Application No. 202180099165.7; First Office Action with English translation dated Mar. 11, 2024; 12 pages.
International Search Report & Written Opinion for International Application No. PCT/EP2021/065649; International Filing Date: Jun. 10, 2021; Date of Mailing: Feb. 25, 2022; 9 pages.
International Search Report & Written Opinion for International Application No. PCT/EP2021/065650; International Filing Date: Jun. 10, 2021; Date of Mailing: Mar. 9, 2022; 9 pages.
U.S. Appl. No. 18/567,851; Non-Final Office Action dated Jun. 17, 2024; 21 pages.

* cited by examiner

SANITARY ARTICLE COMPRISING SHAPING ELEMENTS

CROSS REFERENCE TO RELATED APPLICATIONS

This application is a National Stage Application of PCT/EP2021/065649, filed Jun. 10, 2021, which is incorporated by reference in its entirety herein.

TECHNICAL FIELD

The present disclosure relates to the field of sanitary articles for personal or feminine care. The present disclosure more particularly relates to a sanitary article comprising a topsheet, a backsheet and an absorbent core, wherein a front portion of the absorbent core is provided with a low-density front shaping element for controlled flexible shaping of the sanitary article.

BACKGROUND

Sanitary articles to which this disclosure relates are typically intended to absorb body liquids, such as urine and blood. Users put high demands on such articles, requiring them to be thin, comfortable and at the same time to effectively absorb body liquids.

Disposable sanitary articles, such as sanitary napkins, pantyliners or the like typically include a liquid pervious topsheet, intended to face the wearer during use, a liquid impervious backsheet and an absorbent structure therebetween. Such absorbent structures may be relatively thin and compressed. Absorbent structures being relatively compressed may lose in flexibility and it is important to ensure that these relatively thin and compressed articles absorb liquid quickly, do not leak and are comfortable to wear. One possible solution is to shape the article to have a bowl-shaped structure, such as with channels and elastic elements. However, bowl-shaped structures may be bulky and less body-conforming and thus less discreet. For feminine sanitary napkins the fit is very important for preventing leakage but also so that the sanitary article is discreet to wear.

In view of the above, there is a need for a sanitary article, which has a rapid liquid inlet, improved liquid distribution, good fit and is discreet to wear.

SUMMARY

One or more of the above objects may be achieved with a sanitary article in accordance with claim 1. Further embodiments are set out in the dependent claims, in the following description and in the drawings.

A sanitary article, such as a sanitary napkin or a pantiliner, according to the present disclosure comprises a topsheet, a backsheet, an acquisition layer and an absorbent core. The absorbent core is arranged between the topsheet and the backsheet and the acquisition layer is arranged between the topsheet and the absorbent core. The sanitary article has an extension in a longitudinal direction about a longitudinal centerline and in a transverse direction. The sanitary article has first and second longitudinal side edges extending in the longitudinal direction and front and rear transverse side edges extending in the transverse direction. The sanitary article is divided in a frontmost half and a rearmost half, as seen in the longitudinal direction, wherein the absorbent core in the frontmost half of the sanitary article is provided with a low-density front shaping element having a lower density than an adjacent region of the absorbent core, the low-density front shaping element comprising a shaping element first leg section and a shaping element second leg section. The frontmost half of the sanitary article furthermore comprises a V-shaped, or modified V-shaped, front embossed element comprising a first embossed leg section and a second embossed leg section. The shaping element first leg section and the shaping element second leg section tend towards each other and towards the front transverse side edge of the sanitary article forming a non-intersecting V-shape. The shaping element first leg section and the shaping element second leg section are arranged on a respective side of the longitudinal centerline of the sanitary article. The V-shaped front embossing element is provided only in the topsheet and in the acquisition layer and the low-density front shaping element and the V-shaped front embossing element partly or completely overlap each other.

The term "sanitary article" refers to a product that is placed against the skin of the wearer in the wearer's crotch to absorb and contain body exudates, like urine, faeces and menstrual fluid. The disclosure mainly refers to disposable sanitary articles, which means articles that are not intended to be laundered or otherwise restored or reused as a sanitary article. Examples of disposable sanitary articles include feminine hygiene products such as sanitary napkins, panty liners, incontinence pads and the like.

The term "absorbent core" includes any layer or component, for example absorbent layers or components, arranged between the topsheet/acquisition layer and the backsheet and being intended to distribute or store body exudates. The absorbent core includes any liquid storing layer or layers arranged between the acquisition layer and the backsheet layer.

The sanitary article may comprise a first fastening wing extending at the first longitudinal side edge and a second fastening wing extending at the second longitudinal side edge.

The fastening wings may be provided with attachment means, such as adhesive, for attaching the fastening wings to an undergarment. The fastening wings are intended to be folded around the undergarment and to be attached the undergarment garment on a garment-facing side thereof.

By "modified V-shape" herein is meant that the first and second embossed leg sections may have a connected or non-connected tip portion. If the modified V-shape has a connected tip portion, it may be a rounded tip portion. In a non-connected tip portion, the leg portions may be spaced apart at the tip portion by a distance of for example 1 mm to 10 mm, or 1 mm to 5 mm. The first and second embossed leg sections may furthermore have a respective bend at an end portion, being opposite an intersecting tip portion. The first and second embossed leg sections may thus be straight or slightly bent or curved.

The positioning of the low-density front shaping element may promote a desired upwards, and slightly inwardly, flexing of the front portion conforming to the user body. This arrangement of the low-density front shaping element has been found to improve correct body-conforming shaping of the sanitary article over time as the article is being worn. This may prevent the sanitary article folding in an undesired manner due to movement or due to improper positioning when the user attaches the article in the undergarment. A further advantage of low-density shaping elements, instead of for example compressed shaping elements, is that redistribution of liquid is avoided. However, it has been found that the low-density shaping element may be filled with liquid upon use of the sanitary napkin, which may counteract the shaping of the article. The low-density shaping element may additionally result in a liquid barrier being formed between the crotch portion and the front portion of the absorbent core and thereby reducing the liquid distribution in the absorbent core and the total absorbent capacity of the sanitary napkin. This problem has been overcome, or at least reduced, by the present inventors by providing the low-density shaping element in a non-intersecting V-shape having the shaping element first leg section and the shaping element second leg section according to the present disclosure. This allows liquid distribution between the shaping element first leg section and the shaping element second leg section. To further enhance the liquid distribution and the shaping capability of the low-density shaping element, the topsheet and the acquisition layers are provided with the V-shaped, or modified V-shaped, front embossed element which is partly or completely overlapping with the low-density shaping element. The V-shaped, or modified V-shaped, front embossed element serves to guide the liquid away from the low-density shaping element and some of the liquid over to the low-density shaping element and between the front portion and the crotch portion of the absorbent core.

The first embossed leg section and the second embossed leg section may intersect at a tip portion, the tip portion being aligned with the longitudinal centerline of the sanitary article.

The basis weight of the absorbent core may be at least 20% lower in the low-density front shaping element than in the adjacent region of the absorbent core, optionally at least 40% lower in the low-density front shaping element than in the adjacent region of the absorbent core. The basis weight of the absorbent core may be within the range of from 20% to 80% lower in the low-density front shaping element than in the adjacent region of the absorbent core. This promotes predictable upwards, and slightly inwardly, flexing of the front portion to conform of the absorbent core to the user body. The thickness of the absorbent core in the low-density shaping element may however be the same as in the adjacent region.

The shaping element first leg section and the shaping element second leg section may each have a width within the range of from 0.5 mm to 10 mm, optionally within the range of from 1 mm to 5 mm. This may promote a distinct and predictable flexing at the shaping element in the front portion of the absorbing core.

The first embossed leg section and the second embossed leg section may each have a width within the range of from 1 mm to 5 mm, optionally within the range of from 1.5 mm to 3 mm. This has been seen to promote improved liquid distribution between the front and the crotch region of the absorbent core and also to reduce the risk of the low-density shaping element being filled with liquid.

The absorbent core may have a first and a second longitudinal side edge and the shaping element first leg section may extend to the first longitudinal side edge and the shaping element second leg section extends to the second longitudinal side edge. This may promote a distinct and predictable flexing at the shaping element in the front portion of the absorbing core.

A distance between an inner end point of the shaping element first leg section and an inner end point of the shaping element second leg section may be within the range of from 1 mm to 10 mm, optionally within the range of from 3 mm to 8 mm. Such distance between the inner end points of the shaping elements first and second leg sections provides a predictable upwards, and slightly inward, flexing of the front portion at the tip portion of the shaping element, while allowing liquid distribution between the crotch portion and front portion when needed.

The absorbent core may comprise a head portion, a body portion and a neck portion, the neck portion may form a transitional region between the head portion and the body portion, the head portion being positioned in the frontmost half of the sanitary article and the body portion being positioned in the frontmost half and in the rearmost half of the sanitary article, a transverse width of the absorbent core at the neck region being smaller than a maximum transverse width of the absorbent core in the head portion and in the body portion. The head portion may form a bulging, head shaped, portion in a frontmost third of the absorbent core and the neck portion is a portion in direct connection with the head portion where the absorbent core has a smaller transverse width than in the head portion. The neck portion is the portion having the smallest transverse width in the immediate rearward vicinity of the head portion. If the body portion has a relatively constant width in the frontmost part of the absorbent core, the neck portion may be seen as starting at the smallest transverse width of the absorbent core in direct connection to the head and extending 10 mm rearwardly.

An inner end point of the shaping element first leg section and an inner end point of the shaping element second leg section may be arranged at level with, or not more than 20 mm from, the neck portion, as seen in the longitudinal direction. By "inner end point" is meant the end point of the respective shaping element leg section being closest to the longitudinal centerline of the sanitary article. This may promote lateral flexing of the absorbent core in the groin area of the user.

The first embossed leg section and the second embossed leg may tend towards each other and towards the front transverse side edge of the sanitary article.

The V-shaped front embossing element may completely cover the low-density front shaping element, i.e. the V shaping element first leg section and the V-shaping element second leg section may coincide completely with the first embossed leg section and the second embossed leg section.

The first embossed leg section and the second embossed leg may tend towards each other and towards the rear transverse side edge of the sanitary article.

The first embossed leg section may extend in a direction perpendicular to an extension of the shaping element first leg section and the second embossed leg section extends in a direction perpendicular to an extension of the shaping element second leg section. The first embossed leg section may thus cross the shaping element first leg section and the second embossed leg section may cross the shaping element first leg section. This may promote liquid distribution over the low-density shaping element between the front portion and the crotch portion.

An inner end portion of the shaping element first leg section may coincide with an intermediate segment of the first embossed leg section and the shaping element second leg section coincides with an intermediate segment of the second embossed leg section.

The sanitary article may comprise an embossed crotch functional design element provided only in the topsheet and in the acquisition layer, the embossed crotch functional design element having a boundary comprising a continuous or discontinuous line(s) delimiting an inner crotch region of the embossed crotch functional design element, and the V-shaped front embossing element may constitute a front section of the embossed crotch functional design element.

The embossed functional design element arranged in the crotch region may be provided to provide leakage security and a visual cue for the user of leakage security. It may furthermore flatten the crotch region in a longitudinal edge region of the absorbent core and form a slight upwards bowl shape in the crotch region enabling a closer fit of the absorbent article in the crotch region.

The embossed crotch functional design element may have a first and a second longitudinally extending side section and a rear V-shaped section, wherein a respective first and second leg of the V-shaped section are tending towards the rear edge of the sanitary article and where a distance between the first and the second longitudinally extending side sections increases rearwardly, as seen in the longitudinal direction.

The sanitary article may comprise an outer embossed frame pattern provided in the topsheet and in the acquisition layer, following and extending outboard of an outer perimeter of the absorbent core.

The absorbent core may, in the rearmost half of the sanitary article, be provided with a low-density rear shaping element having a lower density than an adjacent region of the absorbent core, the low-density rear shaping element comprising a shaping element first leg section and a shaping element second leg section tending towards each other and the rear transverse side edge of the sanitary article, thereby forming a non-intersecting V-shape. The shaping element first leg section and the shaping element second leg section are arranged on a respective side of a longitudinal centerline of the sanitary article.

The rearmost half of the sanitary article may comprise a V-shaped rear embossing element comprising a first embossed leg section and a second embossed leg section tending towards each other and the rear transverse side edge of the sanitary article, the V-shaped rear embossing element being provided only in the topsheet and in the acquisition layer. The low-density rear shaping element and the V-shaped rear embossing element partly or completely overlap each other.

BRIEF DESCRIPTION OF THE DRAWINGS

The present invention will be further explained hereinafter by means of non-limiting examples and with reference to the appended drawings wherein.

DETAILED DESCRIPTION

The invention will be described in greater detail below with reference to an exemplary embodiment. The invention may however be embodied in many different forms and should not be construed as being limited to the embodiments set forth in the drawings and the description thereto.

Figure 1:
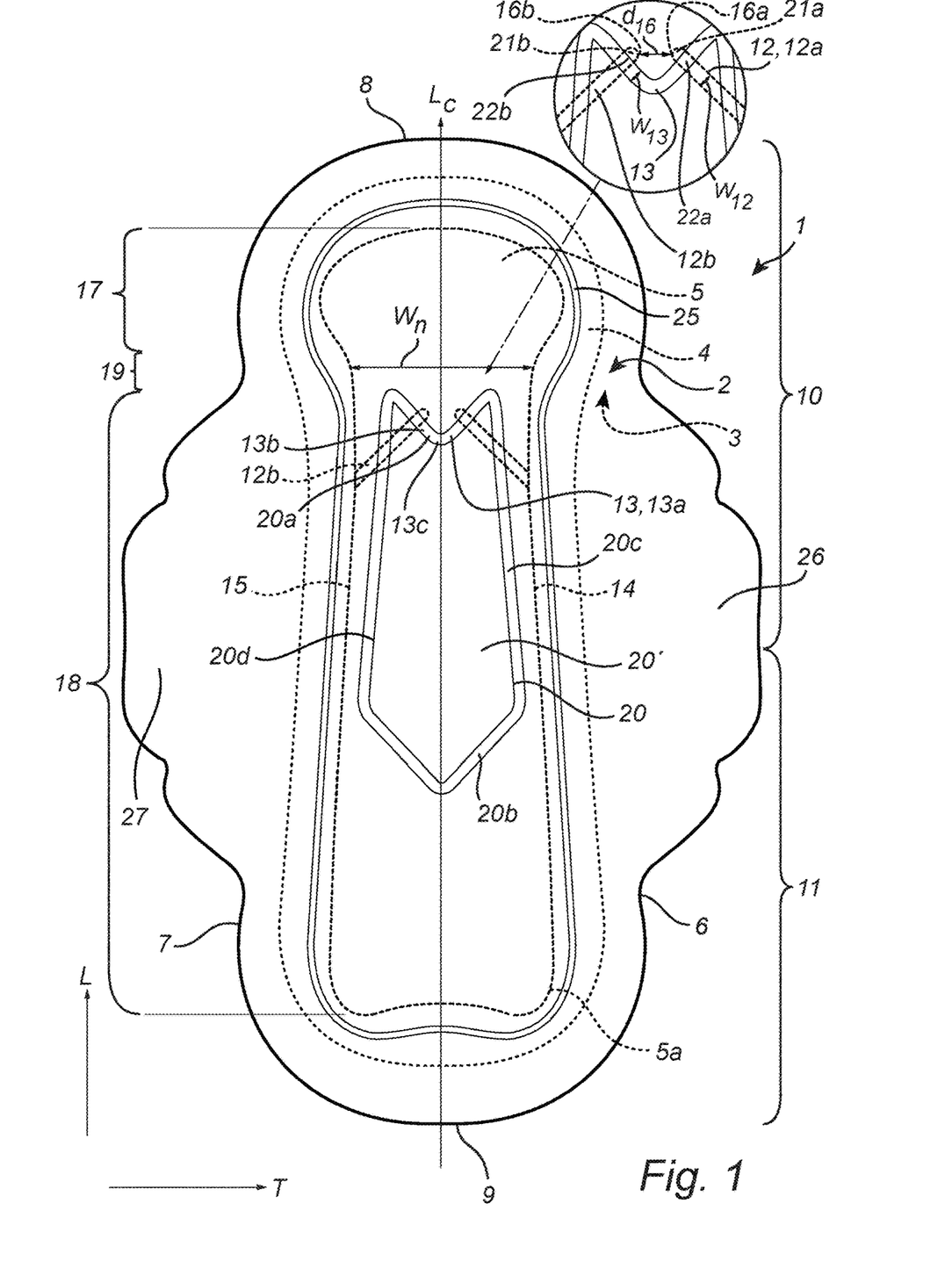
FIG. 1 illustrates a sanitary article according to the present disclosure.

FIG. 1 illustrates a sanitary article 1 according to the present disclosure. The sanitary article 1 comprises a topsheet 2, a backsheet 3, an acquisition layer 4 and an absorbent core 5. The absorbent core 5 is arranged between the topsheet 2 and the backsheet 3 and the acquisition layer 4 is arranged between the topsheet 2 and the absorbent core 5.

The topsheet 2 may include or consist of fibrous nonwoven layer(s) being spunbonded, meltblown, carded, hydroentangled, wetlaid. Suitable nonwoven materials can be composed of natural fibers, such as woodpulp or cotton fibers, synthetic thermoplastic fibers, such as polyolefins, polyesters, polyamides and blends and combinations thereof or from mixtures of natural and synthetic fibers. The materials suited as topshet material should be soft and non-irritating to the skin and be readily penetrated by body fluid, such as menstrual fluid and urine.

The backsheet 3 may consist of a thin plastic film, e.g. a polyethylene or polypropylene film, a nonwoven material coated with a liquid impervious material, a hydrophobic nonwoven, all of which resist liquid penetration. Laminates of plastic films and nonwoven materials may also be used. The backsheet material can be breathable to allow vapor to escape from the absorbent structure, while still preventing liquids from passing through the backsheet material.

The absorbent core 5 constitutes the absorbent structure of the article which acquires and stores bodily fluids. The absorbent core may be of any conventional kind. Examples of commonly occurring absorbent materials are cellulosic fluff pulp, tissue, highly absorbent polymers (so called superabsorbents), absorbent foam materials, absorbent nonwoven materials or the like. It is common to combine cellulosic fluff pulp with superabsorbent polymers in an absorbent core. Superabsorbent polymers are water-swellable, water-insoluble organic or inorganic materials capable of absorbing at least about 20 times their own weight of an aqueous solution containing 0.9 weight percent of sodium chloride. Organic materials suitable for use as a superabsorbent material can include natural materials such as polysaccharides, polypeptides and the like, as well as synthetic materials such as synthetic hydrogel polymers. Such hydrogel polymers include, for example, alkali metal salts of polyacrylic acids, polyacrylamides, polyvinyl alcohol, polyacrylates, polyacrylamides, polyvinyl pyridines, and the like. Other suitable polymers include hydrolyzed acrylonitrile grafted starch, acrylic acid grafted starch, and isobutylene maleic anhydride copolymers and mixtures thereof. The hydrogel polymers are preferably lightly cross-linked to render the material substantially water insoluble. Preferred superabsorbent materials are further surface cross-linked so that the outer surface or shell of the superabsorbent particle, fibre, flake, sphere, etc. possesses a higher crosslink density than the inner portion of the superabsorbent. The superabsorbent materials may be in any form suitable for use in absorbent composites including particles, fibres, flakes, spheres, and the like. A high absorption capacity is provided by the use of high amounts of superabsorbent material. Thin absorbent cores which are common in for example sanitary napkins, baby diapers and incontinence guards, often comprise a compressed, mixed or layered structure of cellulosic fluff pulp and superabsorbent polymers. The size and absorbent capacity of the absorbent core may be varied to suit different product types, such as sanitary napkins for adult incontinent persons or panty liners.

Generally, the core can be of unitary construction, whereby for example the manufacturing process can be simplified. The phrase "unitary construction" in the present context is intended to mean that the absorbent core is constructed from essentially one type of material, this being essentially the same material, or essentially the same combination of two or more materials throughout the absorbent core. Variations in density and concentration of the material may occur, but these are limited to those which may be obtained without incorporation of regions which have been formed separately and then physically joined to each other. For example, when the absorbent core comprises a matrix of hydrophilic fibres and superabsorbent material as described above, the relative concentrations of superabsorbent material and fibres may be different in different parts of the core. However, the absorbent core of unitary construction does not comprise layers or laminates of different composition. Likewise, variations in the density or concentration of various components across the longitudinal direction, the transverse direction or the thickness direction of the absorbent core are acceptable, yet the core should not comprise areas or layers of different composition which are formed separately and later joined together.

A suitable technique for manufacturing the absorbent cores of the present disclosure is mat-forming through an air-laying process. In the process an air-permeable mould is provided. Fibrous material is air-laid into the mould and the mould is filled, whereby an absorbent core is produced with a desired amount of fibrous material.

The sanitary article 1 furthermore comprises an acquisition layer 4 arranged between the absorbent core 5 and the topsheet 2 and being bonded to the topsheet 2 at least by means of embossings. It may however additionally be adhesively attached to the topsheet. The liquid acquisition layer is adapted to quickly receive and temporarily store discharged liquid before it is absorbed by the absorbent core 5. Such acquisition distribution layers may be composed of for example airlaid nonwoven, spunlace nonwoven or high loft nonwoven or foam materials. The nonwoven material may be hydrophilic. A hydrophilic material may be obtained by adding a surfactant.

An air laid nonwoven can be produced with fluff, wood pulp, and here the fluff fibres are dispersed into a fast-moving air stream and condensed onto a moving screen by means of pressure and vacuum. The web can be bonded with resin and/or thermal plastic resin dispersed within the pulp. The web can be thermobonded (by heat), latex bonded (with adhesive) or multibonded (a combination of thermo and latex bonding) or mechanically bonded (high compression and temperature, bonding by hydrogen). The basis weight of the airlaid nonwoven can suitably be from 50 to 100 gsm.

A high loft material is a nonwoven material and may be substantially free from absorbing fibres and superabsorbent material. The high loft nonwoven material may comprise thermoplastic polymer fibres, and may be selected from but not limited to, polyesters, polyamides and polyolefins such as polyethylenes (PE) and polypropylenes (PP), and may be a mixture of any of these. The high loft material refers to low-density bulky fabrics, as compared to flat, paper-like fabrics. High loft webs are characterised by a relatively low density. This means that there is a relatively high amount of void space between the fibres. The high loft nonwoven fibrous layer may typically have a density below 0.200 g/cc (200 kg/m$^3$), in particular ranging from 0.015 g/cc to 0.150 g/cc (15 kg/m$^3$ to 150 kg/m$^3$), in particular from 0.030 g/cc to 0.100 g/cc (30 to 100 kg/m$^3$), for example 0.065 g/cc (65 kg/m$^3$). The average density can be calculated by dividing the basis weight of the high loft layer by its thickness measured at a pressure of 0.5 kPa (see the method details further below). Normally the thickness of high loft materials is more than about 0.5 mm, such as more than 1 mm or suitably 1.5-2.0 mm, and the solid content is low, usually less than 15% by volume. The high loft nonwoven layer may advantageously be a spunmelt nonwoven. Spunmelt is a generic term describing the manufacturing of nonwoven webs directly from thermoplastic polymers. It encompasses two processes and the combination of both: spunlaid (also known as spunbond) nonwoven and meltblown nonwoven. In a spunlaid process, polymer granules are melted and molten polymer is extruded through spinnerets. The continuous filaments are cooled and deposited on to a conveyor to form a uniform web. Some remaining heat can cause filaments to adhere to one another, but this cannot be regarded as the principal method of bonding. The spunlaid process has the advantage of giving nonwovens greater strength, but raw material flexibility is more restricted. Co-extrusion of second components is used in several spunlaid processes, usually to provide extra properties or bonding capabilities. In meltblown web formation, low viscosity polymers are extruded into a high velocity airstream on leaving the spinneret. This scatters the melt, solidifies it and breaks it up into a fibrous web. The liquid acquisition sheet material may be of a spunbonded material and may be a spunbond- meltbond-spunbond (SMS) material. The high loft nonwoven layer may in particular have a thickness ranging from 0.30 mm to 2.00 mm, for example 1.0 mm as measured at a pressure of 0.5 kPa (according to the test method referred to in PCT Application No. PCT/SE2017/050612). The grammage, i.e. basis weight of the high loft material may for example range from 15 gsm to 500 gsm, in particular from 30 gsm to 200 gsm, such as 30-90 gsm, for example 64 gsm.

According to a further variant, the liquid acquisition sheet is a spunlace, also referred to as spunbond, nonwoven material. A spunlace nonwoven product is derived from a process of entangling a web of loose fibres through multiple rows of jets of water at high pressure, this process entangles the fabrics and interlinks the fibres. There are several terms for spunlace nonwoven fabric or spunlaced, such as jet entangled, needled, hydroenentangled or hydraulic, but the term spunlace or spunlaced is the most popular in the nonwoven industry. The raw material for the acquisition sheet can be polypropylene (PP), polyethylene (PE) polyester (PET), polyamide (PA), cellulosic fibres or a combination of these and different weights and compositions are possible, such as viscose, polyester, cotton, nylon and microfibre, wherein viscose is the most commonly used raw material. Thus, if a combination of different fibres is used, this can be a mixture of fibres from different polymers, although each fibre can also include different polymers (e.g. PP/PE bi-component fibres or PP/PE copolymers). The spunlace material usually comprises polypropylene or polyethylene fibres which provide for optimal comfort for the nonwoven material. Other suitable fibres for making the nonwoven material are for example natural fibres such as bamboo, cotton and flax. The grammage of the spunlace nonwoven material can be typically from 30-80 gsm.

The sanitary article 1 has an extension in a longitudinal direction L about a longitudinal centerline $L_c$ and in a transverse direction T, being perpendicular to the longitudinal direction L. The sanitary article 1 is delimited by a first longitudinal side edge 6 and a second longitudinal side edge 7, extending in the longitudinal direction L, and a front transverse side edge 8 and a rear transverse side edge 9, extending in the transverse direction T. The absorbent core 5 has a first longitudinal side edge 14 and a second longitudinal side edge 15.

The sanitary article comprises a first fastening wing 26 extending at the first longitudinal side edge 6 and a second fastening wing 27 extending at the second longitudinal side edge 7.

The sanitary article is divided in a frontmost half 10 and in a rearmost half 11, as seen in the longitudinal direction L, and as measured along the longitudinal centreline $L_c$.

The absorbent core 5 comprises a head portion 17, a body portion 18 and a neck portion 19, the neck portion forming a transitional region between the head portion 17 and the body portion 18. The head portion 17 is positioned in the frontmost half 10 of the sanitary article 1 and the body portion 18 extends both in the frontmost half 10 and in the rearmost half 11 of the sanitary article 1. A transverse width $w_n$ of the absorbent core 5 at the neck region 19 is smaller than a maximum transverse width of the absorbent core 5 in the head portion 17 and in the body portion 18.

The sanitary article 1 is, in its frontmost half 10, provided with a low-density front shaping element 12 in the absorbent core 5, the low-density front shaping element 12 having a lower density than an adjacent region in the absorbent core 5. The low-density front shaping element 12 comprises a shaping element first leg section 12a and a shaping element second leg section 12b. The absorbent core 5 may have a basis weight being at least 20% lower in the low-density front shaping element 12 than in the adjacent region of the absorbent core 5, optionally at least 40% or 50%, such as from 20% to 80% lower in the low-density front shaping element 12 than in the adjacent region of the absorbent core 5. The shaping element first leg section 12a and the shaping element second leg section 12b may each has a width $W_{12}$ within the range of from 0.5 mm to 5 mm.

The frontmost half 10 of the sanitary article 1 furthermore comprises a V-shaped front embossed element 13 comprising a first embossed leg section 13a and a second embossed leg section 13b. The V-shaped front embossed element 13 is provided only in the topsheet 2 and in the acquisition layer 4 and points towards the rear transverse side edge 9 of the sanitary article 1. The first embossed leg section 13a extends in a direction perpendicular to an extension of the shaping element first leg section 12a and the second embossed leg section 13b extends in a direction perpendicular to an extension of the shaping element second leg section 13a, with an inner end portion 21a of the shaping element first leg section 12a coinciding with an intermediate segment 22a of the first embossed leg section 13a and the shaping element second leg section 12b coinciding with an intermediate segment 22b of the second embossed leg section 13b. The first embossed leg section 13a thus crosses the shaping element first leg section 12a and the second embossed leg section 13b crosses the shaping element first leg section 12b. This may promote liquid distribution over the low-density shaping element 12 between a front portion and a crotch portion of the sanitary article 1.

In this FIG. 1, the embossed element is a V-shape shape embossed element 13. However, the front embossed element 13 may alternatively have a modified V-shape, which means that the first and second embossed leg sections may have a connected or non-connected tip portion. If the modified V-shape has a connected tip portion, it may be a rounded tip portion. In a non-connected tip portion the leg portions may be spaced apart at the tip portion by a distance of for example 1 mm to 10 mm, or 1 mm to 5 mm. The first and second embossed leg sections 13a, 13b may furthermore have a respective bend at an end portion, being opposite an intersecting tip portion. The first and second embossed leg sections may thus be straight or slightly bent or curved.

The first embossed leg section 13a and the second embossed leg section 13b intersect at a tip portion 13c, the tip portion 13c being aligned with the longitudinal centerline $L_c$ of the sanitary article 1. The first embossed leg section 13a and the second embossed leg section 13b may each have a width $W_{13}$ within the range of from 1 mm to 5 mm.

The shaping element first leg section 12a and the shaping element second leg section 12b tend towards each other and towards the front transverse side edge 8 of the sanitary article 1 to form a non-intersecting V-shape. The shaping element first leg section 12a and the shaping element second leg section 12b are arranged on a respective side of the longitudinal centerline $L_c$ of the sanitary article 1 with a distance $d_{16}$ between an inner end point 16a of the shaping element first leg section 12a and an inner end point 16b of the shaping element second leg section 12b. The distance $d_{16}$ may be within the range of from 1 mm to 10 mm.

The shaping element first leg section 12a extends to the first longitudinal side edge 14 of the absorbent core 5 and the shaping element second leg section 12b extends to the second longitudinal side edge 15 of the absorbent core 5. This enhances the inwards and upwards folding in the frontmost half of the absorbent core 5 at the front low-density shaping element 12.

The sanitary article 1 in FIG. 1 furthermore comprises an embossed crotch functional design element 20 provided only in the topsheet 2 and in the acquisition layer 4. The embossed crotch functional design element 20 has a boundary comprising a continuous or discontinuous line(s) delimiting an inner crotch region 20' of the embossed crotch functional design element 20, the embossed crotch functional design element 20 comprising a rear V-shaped section 20b with a tip portion pointing towards the rear transverse side edge 9 of the sanitary article 1. The V-shaped front embossing element 13 constitutes a front section 20a of the embossed crotch functional design element 20. The embossed crotch functional design element 20 furthermore has a first and a second longitudinally extending side section 20c, 20d extending between the front section 20a and the rear section 20b on a respective side of the inner crotch region 20' of the embossed crotch functional design element 20.

The sanitary article 1 furthermore comprises an outer embossed frame pattern 25 provided in the topsheet 2 and in the acquisition layer 4, following and extending outboard of the periphery 5a of the absorbent core 5.

Figure 2:
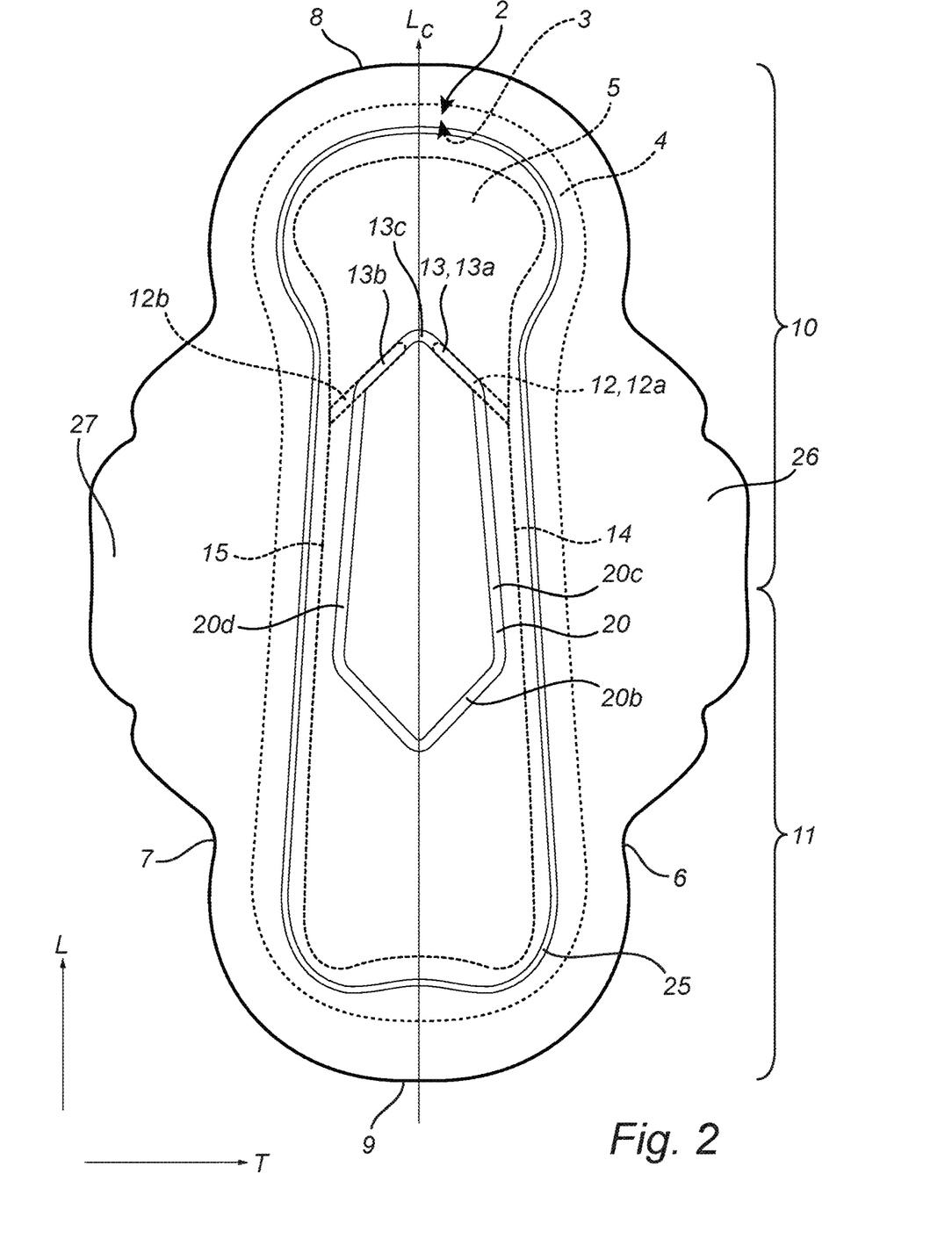
FIG. 2 illustrates an alternative sanitary article according to the present disclosure.

FIG. 2 illustrates an alternative sanitary article 1 according to the present disclosure. The sanitary article 1 comprises a topsheet 2, a backsheet 3, an acquisition layer 4 and an absorbent core 5. The absorbent core 5 is arranged between the topsheet 2 and the backsheet 3 and the acquisition layer 4 is arranged between the topsheet 2 and the absorbent core 5.

The sanitary article 1 has an extension in a longitudinal direction L about a longitudinal centerline $L_c$ and in a transverse direction T. The sanitary article 1 comprises first and second longitudinal side edges 6, 7, extending in the longitudinal direction L, and a front transverse side edge 8 and a rear transverse side edge 9, extending in the transverse direction T. The absorbent core 5 has a first longitudinal side edge 14 and a second longitudinal side edge 15.

The sanitary article comprises a first fastening wing 26 extending at the first longitudinal side edge 6 and a second fastening wing 27 extending at the second longitudinal side edge 7.

The sanitary article is divided in a frontmost half 10 and in a rearmost half 11, as seen in the longitudinal direction L, and as measured along the longitudinal centreline $L_c$. The sanitary article 1 is, in its frontmost half 10, provided with a low-density front shaping element 12 in the absorbent core 5. The low-density front shaping element 12 has a lower density than an adjacent region in the absorbent core 5.

The low-density front shaping element 12 comprises a shaping element first leg section 12a and a shaping element second leg section 12b. The frontmost half 10 of the sanitary article 1 furthermore comprises a V-shaped front embossed element 13 comprising a first embossed leg section 13a and a second embossed leg section 13b.

The V-shaped front embossed element 13 is provided only in the topsheet 2 and in the acquisition layer 4 and points towards the front transverse side edge 8 of the sanitary article 1. The low-density front shaping element 12 and the V-shaped front embossed element 13 overlap each other such that at least 60% of the low-density front shaping element 12 is covered by the V-shaped front embossed element 13.

In FIG. 2, the embossed element is a V-shaped front embossed element 13, however, the front embossed element 13 may alternatively have a modified V-shape, which means that the first and second embossed leg sections may have a connected or non-connected tip portion. If the modified V-shape has a connected tip portion, it may be a rounded tip portion. In a non-connected tip portion, the leg portions may be spaced apart at the tip portion by a distance of, for example, 1 mm to 10 mm, or 1 mm to 5 mm.

The first embossed leg section 13a and the second embossed leg section 13b intersect at a tip portion 13c, the tip portion 13c being aligned with the longitudinal centerline $L_c$ of the sanitary article 1.

The shaping element first leg section 12a extends to the first longitudinal side edge 14 of the absorbent core 5 and the shaping element second leg section 12b extends to the second longitudinal side edge 15 of the absorbent core 5. This enhances the upwards folding in the rearmost half of the absorbent core 5 at the rear low-density shaping element 12.

The sanitary article 1 in FIG. 2 furthermore comprises an embossed crotch functional design element 20 provided only in the topsheet 2 and in the acquisition layer 4. The embossed crotch functional design element 20 comprises a rear V-shaped section 20b pointing towards the rear transverse side edge 9 of the sanitary article 1.

The embossed crotch functional design element 20 furthermore has a first and a second longitudinally extending side section 20c, 20d.

Figure 3:
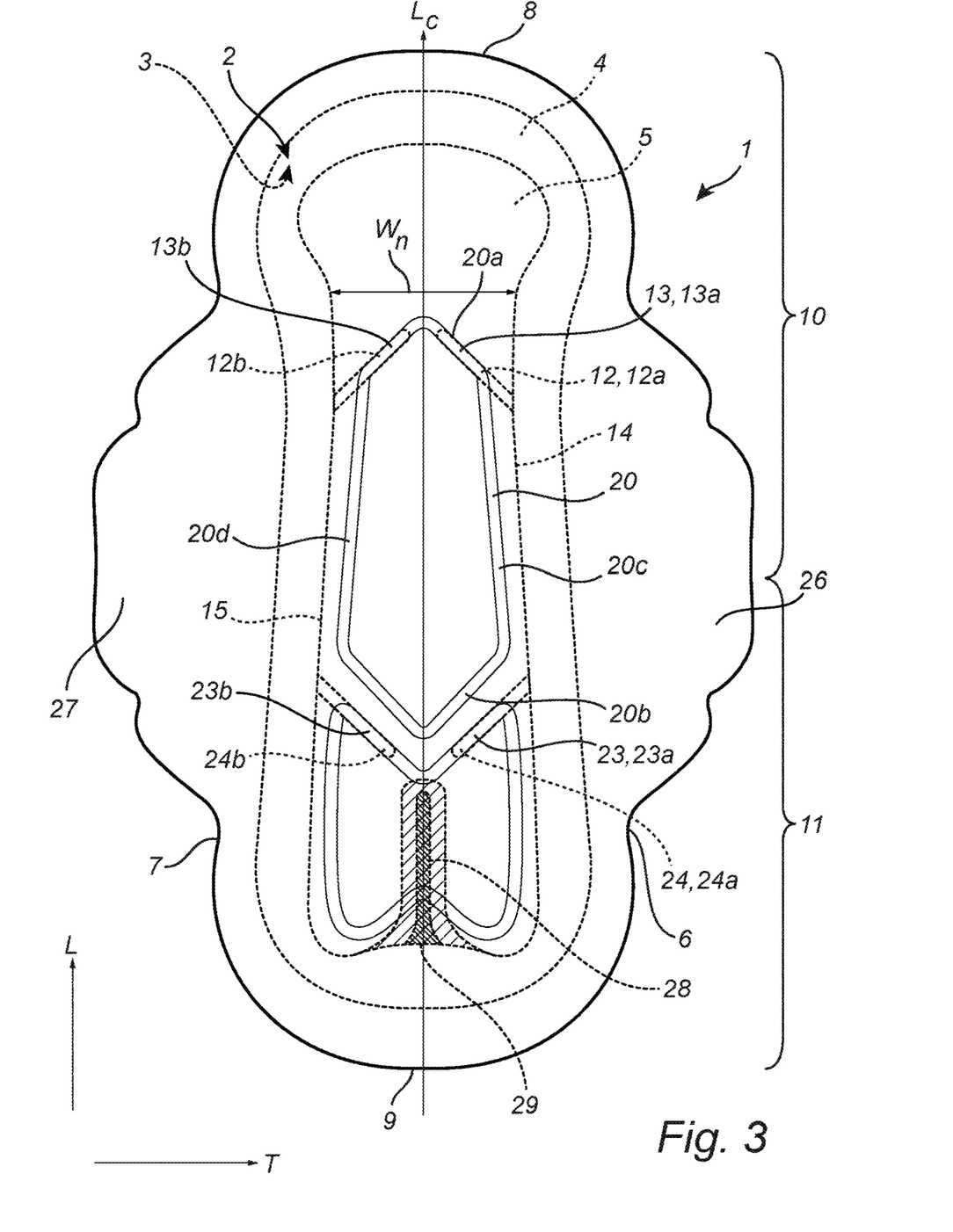
FIG. 3 illustrates a further sanitary article according to the present disclosure.

FIG. 3 illustrates an alternative sanitary article 1 according to the present disclosure. The sanitary article 1 comprises a topsheet 2, a backsheet 3, an acquisition layer 4 and an absorbent core 5. The absorbent core 5 is arranged between the topsheet 2 and the backsheet 3 and the acquisition layer 4 is arranged between the topsheet 2 and the absorbent core 5.

The sanitary article 1 has an extension in a longitudinal direction L about a longitudinal centerline $L_c$ and in a transverse direction T. The sanitary article 1 comprises first and second longitudinal side edges 6, 7, extending in the longitudinal direction L, and a front transverse side edge 8 and a rear transverse side edge 9, extending in the transverse direction T. The absorbent core 5 has a first longitudinal side edge 14 and a second longitudinal side edge 15.

The sanitary article is divided in a frontmost half 10 and in a rearmost half 11, as seen in the longitudinal direction L. The sanitary article 1 is, in its frontmost half 10, provided with a low-density front shaping element 12 in the absorbent core 5. The low-density front shaping element 12 has a lower density than an adjacent region in the absorbent core 5.

The low-density front shaping element 12 comprises a shaping element first leg section 12a and a shaping element second leg section 12b. The frontmost half 10 of the sanitary article 1 furthermore comprises a V-shaped front embossed element 13 comprising a first embossed leg section 13a and a second embossed leg section 13b.

The V-shaped front embossed element 13 is provided only in the topsheet 2 and in the acquisition layer 4 and the first embossed leg section 13a and the second embossed leg 13b tend towards each other and towards the rear transverse side edge 9 of the sanitary article 1.

The low-density front shaping element 12 and the V-shaped front embossed element 13 overlap each other such that at least 60% of the low-density front shaping element 12 is covered by the V-shaped front embossed element 13.

The sanitary article 1 in FIG. 3 furthermore comprises an embossed crotch functional design element 20 provided only in the topsheet 2 and in the acquisition layer 4. The embossed crotch functional design element 20 comprises a rear V-shaped section 20b, with a converging tip portion pointing towards the rear transverse side edge 9 of the sanitary article 1. The embossed crotch functional design element 20 furthermore has a first and a second longitudinally extending side section 20c, 20d In FIG. 3 the absorbent core 5 is provided with a low-density rear shaping element 24 in the rearmost half 11 of the sanitary article 1, the low-density rear shaping element 24 having a lower density than an adjacent region in the absorbent core 5. The low-density rear shaping element 24 comprises a shaping element first leg section 24a and a shaping element second leg section 24b tending towards each other and towards the rear transverse side edge 9 of the sanitary article 1 forming a non-intersecting V-shape.

The rearmost half 11 of the sanitary article 1 furthermore comprises a V-shaped rear embossed element 23 comprising a first embossed leg section 23a and a second embossed leg section 23b. The first embossed leg section 23a and the second embossed leg section 23b tend towards each other and towards the rear transverse side edge 9 of the sanitary article 1.

The V-shaped rear embossed element 23 is provided only in the topsheet 2 and in the acquisition layer 4. The low-density rear shaping element 24 and the V-shaped rear embossed element 23 partly overlap each other, such that between 50 to 75% of the low-density rear shaping element 24 is covered by the V-shaped rear embossed element 23.

Along the longitudinal centerline $L_c$ of the sanitary article 1, the absorbent core 5 is provided with a low-density rear central region 28 extending in the longitudinal direction L. The low-density rear central region 28 is arranged rearwardly of the low-density rear shaping element 24. The low-density rear central region 28 extends to a rear transverse edge 29 of the absorbent core 5. The low-density rear central region 28 has a density gradient with lower density at the longitudinal centerline $L_c$ of the sanitary article 1 and an increasing density, as seen in the transverse direction T towards the respective first and second longitudinal side edge 14, 15 of the absorbent core 5.

Figure 4:
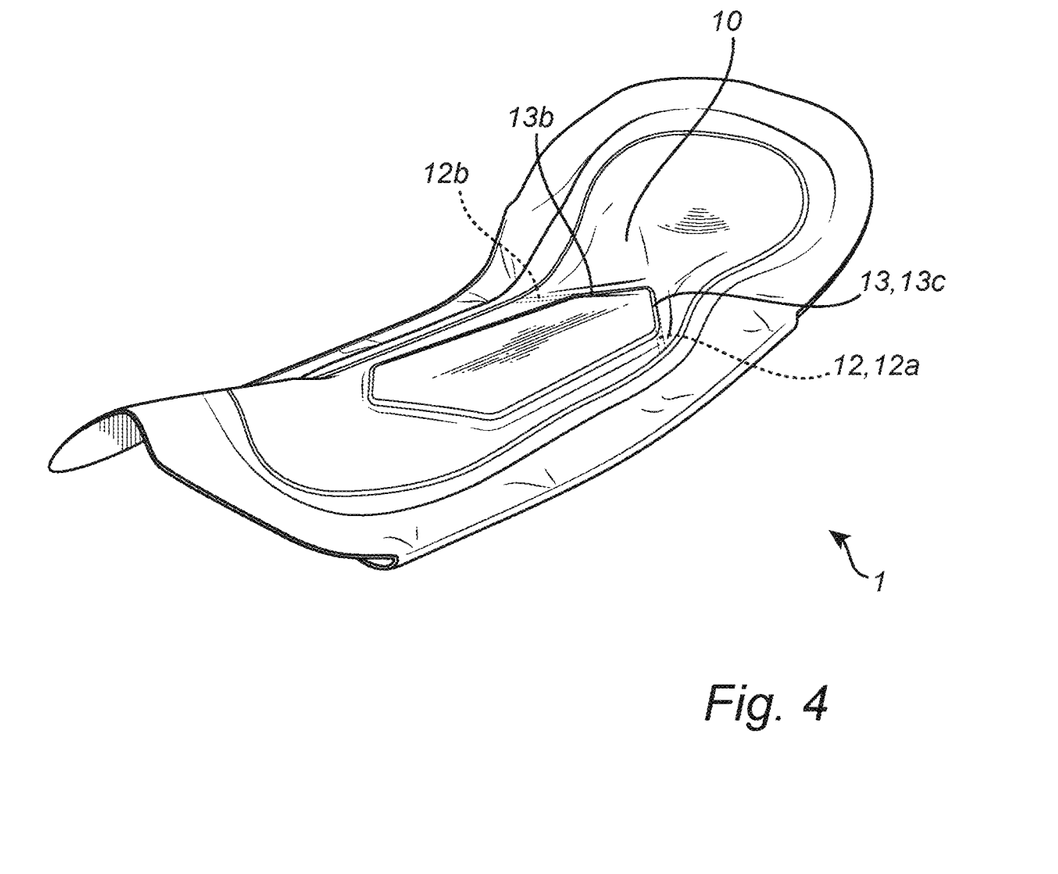
FIG. 4 illustrates shaping of the sanitary article according to FIG. 1 during use.

FIG. 4 illustrates the sanitary article 1 from FIG. 1 when being placed in an undergarment of a user. The low-density front shaping element 12 in the absorbent core 5 (not shown) comprising the shaping element first leg section 12a and the shaping element second leg section 12b facilitates a predictable upwardly and slightly inwardly flexing of the frontmost half 10 of the sanitary article 1 is in a controlled manner. When being placed in an undergarment, the sanitary article 1 will follow the contour of the user by flexing the article upwardly and will also raise the longitudinal side portions of the sanitary article 1 in the frontmost half 10 under the influence of the forces exerted on the sanitary article 1 by the user's undergarment and by the user's legs to provide the article with a body-conforming shape protecting the article from side leakages and quickly conveying liquid to a crotch portion region of the sanitary article 1. The frontmost half 10 of the sanitary article 1 furthermore comprises the V-shaped front embossed element 13 comprising a first embossed leg section 13a and a second embossed leg section 13b. The V-shaped front embossed element 13 improves the liquid distribution between the crotch region and the front region of the sanitary article 1 and may prevent liquid from filling up the low-density shaping element 12 and thus prevent folding of the sanitary article 1 in the desired manner.

The invention claimed is:

1. A sanitary article comprising a topsheet, a backsheet, an acquisition layer and an absorbent core, the absorbent core being arranged between the topsheet and the backsheet and the acquisition layer being arranged between the topsheet and the absorbent core, the sanitary article having an extension in a longitudinal direction about a longitudinal centerline and in a transverse direction, the sanitary article having first and second longitudinal side edges extending in the longitudinal direction and front and rear transverse side edges extending in the transverse direction, the sanitary article being divided in a frontmost half and a rearmost half, as seen in the longitudinal direction, wherein the absorbent core in the frontmost half of the sanitary article is provided with a low-density front shaping element having a lower density than an adjacent region of the absorbent core, the low-density front shaping element comprising a shaping element first leg section and a shaping element second leg section, the frontmost half of the sanitary article furthermore comprising a V-shaped, or modified V-shaped, front embossed element comprising a first embossed leg section and a second embossed leg section, wherein the shaping element first leg section and the shaping element second leg section tend towards each other and towards the front transverse side edge of the sanitary article to form a non-intersecting V-shape, the shaping element first leg section and the shaping element second leg section being arranged on a respective side of the longitudinal centerline of the sanitary article, and in that the V-shaped front embossing element is provided only in the topsheet and in the acquisition layer and in that the low-density front shaping element and the V-shaped front embossing element partly or completely overlap each other.

2. The sanitary article according to claim 1, wherein the first embossed leg section and the second embossed leg section intersect at a tip portion, the tip portion being aligned with the longitudinal centerline of the sanitary article.

3. The sanitary article according to claim 1, wherein the absorbent core has a basis weight being at least 20% lower in the low-density front shaping element than in the adjacent region of the absorbent core, optionally at least 40% lower in the low-density front shaping element than in the adjacent region of the absorbent core.

4. The sanitary article according to claim 1, wherein the shaping element first leg section and the shaping element second leg section each has a width within the range of from 0.5 mm to 10 mm.

5. The sanitary article according to claim 1, wherein the first embossed leg section and the second embossed leg section each has a width within the range of from 1 mm to 5 mm.

6. The sanitary article according to claim 1, wherein the absorbent core has a first and a second longitudinal side edge and wherein the shaping element first leg section extends to the first longitudinal side edge and the shaping element second leg section extends to the second longitudinal side edge.

7. The sanitary article according to claim 1, wherein a distance between an inner end point of the shaping element first leg section and an inner end point of the shaping element second leg section is within the range of from 1 mm to 10 mm.

8. The sanitary article according to claim 1, wherein the absorbent core comprises a head portion, a body portion and a neck portion, the neck portion forming a transitional region between the head portion and the body portion, the head portion being positioned in the frontmost half of the sanitary article and the body portion being positioned in the frontmost half and in the rearmost half of the sanitary article, wherein a transverse width of the absorbent core at the neck region is smaller than a maximum transverse width of the absorbent core in the head portion and in the body portion.

9. The sanitary article according to claim 8, wherein an inner end point of the shaping element first leg section and an inner end point of the shaping element second leg section is arranged at level with, or not more than 20 mm from, the neck portion, as seen in the longitudinal direction.

10. The sanitary article according to claim 1, wherein the first embossed leg section and the second embossed leg tend towards each other and towards the front transverse side edge of the sanitary article.

11. The sanitary article according to claim 10, wherein the V-shaped front embossing element completely covers the low-density front shaping element.

12. The sanitary article according to claim 1, wherein the first embossed leg section and the second embossed leg tend towards each other and towards the rear transverse side edge of the sanitary article.

13. The sanitary article according to claim 12, wherein the first embossed leg section extends in a direction perpendicular to an extension of the shaping element first leg section and wherein the second embossed leg section extends in a direction perpendicular to an extension of the shaping element second leg section.

14. The sanitary article according to claim 12, wherein an inner end portion of the shaping element first leg section coincides with an intermediate segment of the first embossed leg section and the shaping element second leg section coincides with an intermediate segment of the second embossed leg section.

15. The sanitary article according to claim 1, wherein the sanitary article comprises an embossed crotch functional design element provided only in the topsheet and in the acquisition layer, the embossed crotch functional design element having a boundary comprising a continuous or discontinuous line(s) delimiting an inner crotch region of the embossed crotch functional design element, and wherein the V-shaped front embossing element constitutes a front section of the embossed crotch functional design element.

16. The sanitary article according to claim 15, wherein the embossed crotch functional design element has a first and a second longitudinally extending side section and a rear V-shaped section pointing towards the rear edge of the sanitary article and where a distance between the first and the second longitudinally extending side sections increases rearwardly, as seen in the longitudinal direction.

17. The sanitary article according to claim 1, wherein the sanitary article comprises an outer embossed frame pattern provided in the topsheet and in the acquisition layer, following and extending outboard of an outer perimeter of the absorbent core.

18. The sanitary article according to claim 1, wherein the absorbent core in the rearmost half of the sanitary article is provided with a low-density rear shaping element having a lower density than an adjacent region of the absorbent core, the low-density rear shaping element comprises a shaping element first leg section and a shaping element second leg section tending towards each other and the rear transverse side edge of the sanitary article and forming a non-intersecting V-shape, the shaping element first leg section and the shaping element second leg section being arranged on a respective side of a longitudinal centerline of the sanitary article.

19. The sanitary article according to claim 18, wherein the rearmost half of the sanitary article comprises a V-shaped rear embossing element comprising a first embossed leg section and a second embossed leg section tending towards each other and the rear transverse side edge of the sanitary article, the V-shaped rear embossing element being provided only in the topsheet and in the acquisition layer, the low-density rear shaping element and the V-shaped rear embossing element partly or completely coinciding with each other.

* * * * *